(12) United States Patent
Miltner et al.

(10) Patent No.: US 8,977,505 B2
(45) Date of Patent: Mar. 10, 2015

(54) HAND HELD ANALYSIS DEVICE FOR ANALYZING A BODY FLUID AND A CONTROL METHOD THEREFOR

(75) Inventors: Karl Miltner, Frankenthal (DE); Thorsten Baeter, Warsaw (PL); Gerhard Frisch, Edingen-Neckarhausen (DE); Sebastian Liedtke, Heidelberg (DE); Wilfried Schmid, Mannheim (DE); Wolfgang Heck, Frankenthal (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1086 days.

(21) Appl. No.: 12/974,816

(22) Filed: Dec. 21, 2010

(65) Prior Publication Data

US 2012/0004852 A1  Jan. 5, 2012

Related U.S. Application Data

(63) Continuation of application No. PCT/EP2009/057666, filed on Jun. 19, 2009.

(30) Foreign Application Priority Data

Jun. 25, 2008 (EP) .................................. 08158943

(51) Int. Cl.
G01N 33/487 (2006.01)
G01N 35/00 (2006.01)

(52) U.S. Cl.
CPC .... *G01N 33/48764* (2013.01); *G01N 35/00009* (2013.01)
USPC ............................................. 702/19; 422/66

(58) Field of Classification Search
CPC .................... G01N 33/48764; G01N 33/4875; G01N 33/48; G01N 33/483; G01N 35/00009
USPC ........................ 702/120, 19; 422/66; 436/44
See application file for complete search history.

(56) References Cited

U.S. PATENT DOCUMENTS

| | | | |
|---|---|---|---|
| 4,685,059 A | 8/1987 | Yamamoto | |
| 2004/0059316 A1* | 3/2004 | Smedegaard | ............ 604/890.1 |
| 2006/0079811 A1* | 4/2006 | Roe et al. | ..................... 600/583 |
| 2006/0216817 A1 | 9/2006 | Hoenes et al. | |
| 2007/0020143 A1 | 1/2007 | Seidenstricker et al. | |
| 2007/0077175 A1 | 4/2007 | Harttig | |
| 2009/0200413 A1 | 8/2009 | Sacherer | |

FOREIGN PATENT DOCUMENTS

| | | |
|---|---|---|
| CN | 1822792 A | 8/2006 |
| CN | 1833610 A | 9/2006 |
| EP | 1739432 A1 | 1/2007 |
| EP | 1889570 A2 | 2/2008 |

(Continued)

*Primary Examiner* — Jonathan C Teixeira Moffat
*Assistant Examiner* — Liam R Casey
(74) *Attorney, Agent, or Firm* — Roche Diagnostics Operatins, Inc.

(57) ABSTRACT

A method is provided for controlling a hand-held analysis device for analyzing a body fluid in which in each case at least one test means for single use is automatically provided in consecutive measuring cycles by means of a control device where each measuring cycle in a measuring mode of the control device is triggered by a start actuation. According to the invention it is proposed that a defined control intervention puts the control device into a maintenance mode in which the automatic provision of a test means is prevented.

12 Claims, 2 Drawing Sheets

(56) References Cited

FOREIGN PATENT DOCUMENTS

| | | | |
|---|---|---|---|
| EP | 1770395 B1 | 11/2010 |
| JP | 2004-205319 A | 7/2004 |
| JP | 2006-084367 A | 3/2006 |
| WO | 2007/090662 A1 | 8/2007 |
| WO | 2008/022999 A1 | 2/2008 |

* cited by examiner

HAND HELD ANALYSIS DEVICE FOR ANALYZING A BODY FLUID AND A CONTROL METHOD THEREFOR

CLAIM OF PRIORITY

The present application is a continuation application based on and claiming priority to PCT/EP2009/057666, filed Jun. 19, 2009, which claims the priority benefit of European Patent Application No. 08158943.4, filed Jun. 25, 2008, each of which are hereby incorporated by reference in their respective entireties.

TECHNICAL FIELD OF THE INVENTION

The present application relates to a method for controlling a hand-held analysis device for analyzing a body fluid, and more particularly to such a device in which in each case at least one test means for single use is automatically provided in consecutive measuring cycles by means of a control device implemented in the analysis device, wherein with the control device in a measuring mode, a measuring cycle is triggered by a start actuation. The present application additionally concerns a hand-held analysis device for analyzing blood sugar.

BACKGROUND

Methods have been disclosed in which individual test strips are supplied from an exchangeable drum magazine for analytical purposes. Consumption of the individual test strips is recorded by the device by assigning a counter reading to a magazine identifier and is not written back onto the magazine thus also simplifying the optional use of partially used magazines. See, for example, a system such as is disclosed in EP-A 1 770 395.

In order to further increase the system integration, in other disclosures it has been proposed to use a spooled test tape with analytical test fields that are spaced apart as test means in a hand-held device instead of individual strips. Marker areas which allow an exact positioning of the test fields are provided in this case to register the distance travelled during tape transport. With such concepts it is particularly challenging to minimize the overall size and the number of required operating steps. See, for example, a system such as is disclosed in EP-A 1 739 432.

The object of the invention is to further develop the methods and products known in the prior art and to increase the user-friendliness and reliability of the methods using simple means also with regard to an optimized utilization of the test means.

SUMMARY

This object and others that will be appreciated by a person of ordinary skill in the art have been achieved according to the embodiments of the present invention disclosed herein, including those set forth in the claims.

It has been noted by the inventors that the provision of an analytical test means in a hand-held device cannot usually be retracted without diminishing the test quality. This problem is comparable with conventional film cameras which should not simply be opened when a film has been placed in them. In order to achieve the object of the present invention, in one embodiment, the present invention comprises a defined control intervention that puts the device-implemented program-controlled control device into a maintenance mode in which the automatic provision of a test means inserted into the device is prevented. In this manner an unintentional test loss is avoided without impairing the handling in a normal measuring process.

In one embodiment, a method is performed for controlling a hand-held analysis device for analyzing a body fluid, the device comprising an electronic control device configured to automatically provide at least one test means for a single use in consecutive measuring cycles when the control device is in a measuring mode, each measuring cycle being triggered by a start actuation, the test means comprising a wound test tape, the method comprising the step of putting the control device into a maintenance mode by a defined control intervention, wherein the automatic provision of a test means is suspended during the maintenance mode so that the automatic provision of the test means in the hand-held analysis device is prevented.

The start of a measuring cycle is blocked in the maintenance mode even in the case of a start actuation. This allows handling steps to be carried out which in the measuring mode would have led to a start of a measurement.

The maintenance mode is established to enable the device to be cleaned or to allow an exchange of test means or an intermittent removal of the test means out of the device without loss of test means due to an unintentional test provision.

In order to reduce the constructional complexity, in one embodiment the maintenance mode is selected by a user via a software menu of the electronic control device. This can be achieved in a particularly simple manner when the maintenance mode is initiated by a manually operated switch such as a softkey provided on the device.

In another embodiment, a predetermined operation of a device component is recognized by the control device as a start actuation. This allows the number of required operating steps to be reduced and achieves a rapid availability. In further refinements, the start actuation and/or an exchange of test means is monitored by a sensor, and the sensor signal is ignored when the control device is in the maintenance mode.

In other embodiments, the test means are protected in a housing of the hand-held analysis device against environmental influences such as moisture in order to ensure a high degree of reliability.

In yet other embodiments, improved operating friendliness is achieved when measuring cycles are configured to be triggered by the opening of a protective cover of the hand-held analysis device whereupon a test means is provided for access by the user.

In embodiments in which test means stored in magazines are used, one refinement when in the measuring mode provides that the test means are transported by a transport device to at least one predetermined position and when the automatic transport of test means is suspended in the maintenance mode. According to a further refinement the respective test means is transported from a store of test means to an application site and optionally to a test means waste during a measuring cycle.

Embodiments of the present invention can be used for example in connection with using a test tape furnished with a plurality of analytical test fields and/or lancing elements as test means and winding on the test tape in sections in order to provide the test means. A further refinement provides that the test means can be exchanged in a compartment of the device such as in the form of a magazine or cassette, and that a test means activated by a start actuation is discarded in the measuring mode when the compartment of the device is opened.

The present invention also concerns a device for carrying out the method, comprising a control device configured for automatically providing test means designed for single use in consecutive measuring cycles where each measuring cycle can be triggered in a measuring mode of the control device by a start actuation and where a defined control intervention can put the control device into a maintenance mode in which the automatic provision of a test means is prevented.

The present invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
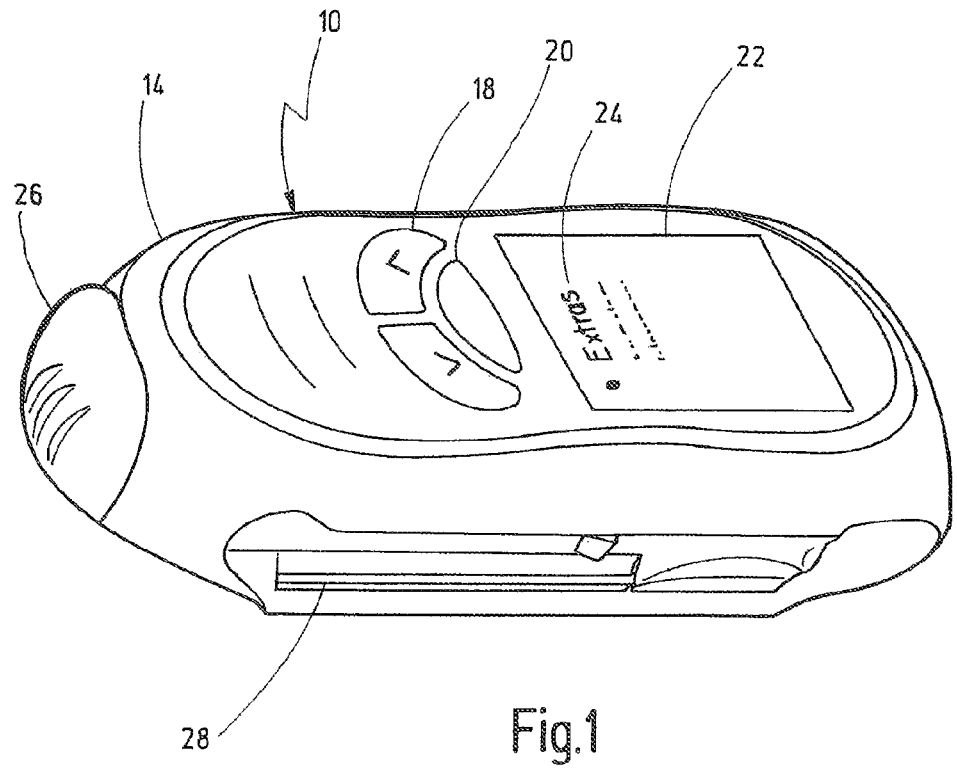
FIG. 1 shows a perspective view of a portable blood sugar measuring device configured for use with a test tape cassette.
Figure 2:
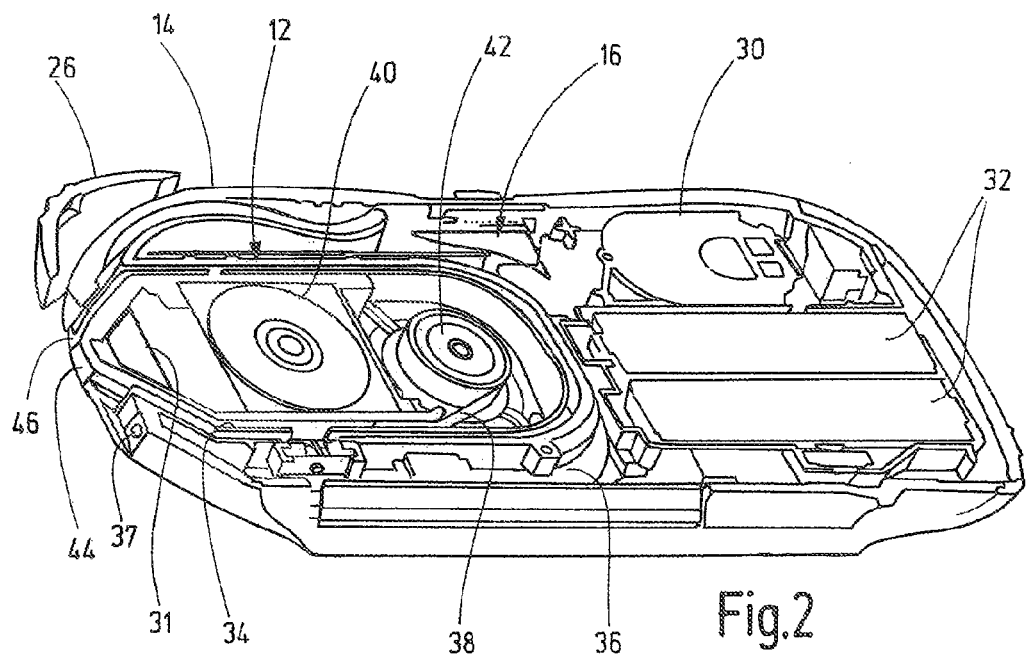
FIG. 2 shows the measuring device according to FIG. 1 in a longitudinal section.

The portable blood sugar measuring device 10 shown in FIGS. 1 and 2 allows a user to determine his own blood sugar level on the spot in a substantially automated measuring process. In this connection a plurality of analytical test means in the form of a tape cassette 12 as an exchangeable disposable can be inserted into the compact device housing 14 in order to carry out a corresponding number of tests without complicated handling. For the device maintenance it is possible to prevent an unintentional loss of test means by an advantageous process control by means of an electronic control device 16 of the device 10 provided with a control software.

As shown in FIG. 1 various control buttons 18, 20 are arranged on the top side of the housing 14 for manual actuation. A screen 22 enables operating menus 24 and measurement results to be displayed. The tape cassette 12 protected in the housing 14 is accessible at an application site for the application of a blood sample by opening a protective cover 26. A lancing aid (not shown) for collecting the blood sample can be flange-mounted on a holder 28 at the side of the housing 14.

FIG. 2 shows a section through the interior of the device with an inserted tape cassette 12, control device (circuit board 16), tape drive unit 30, measuring unit 31 and energy supply (batteries 32). The cassette 12 stored in the cassette compartment 34 can be exchanged as a consumable article via a cover 36 at the bottom of the housing. The position of the various device access points is registered by sensors as shown for the protective cover 26 as an example by the switch 37.

The cassette 12 comprises a test tape 38, a supply spool 40 which is sealed towards the outside for unwinding unused test tape and a take-up spool 42 to wind on used test tape. Test fields 44 coated with a test chemistry are mounted spaced apart from one another on the test tape 38 as test means for detecting the analyte (e.g., glucose). Alternatively or in addition it is also possible to store lancing elements that are not shown on a carrier tape for a skin puncture. The test tape 38 can be wound forwards by means of the drive unit 30 such that the test units 20 can be provided successively at an application site 46 for applying the blood sample, where said application site (46) is uncovered by swinging back the protective cover 26. A glucose measurement value can then be obtained by a reflectometric measurement from the rear side of the test field 44 to which blood has been applied on the basis of a color change.

Figure 3:
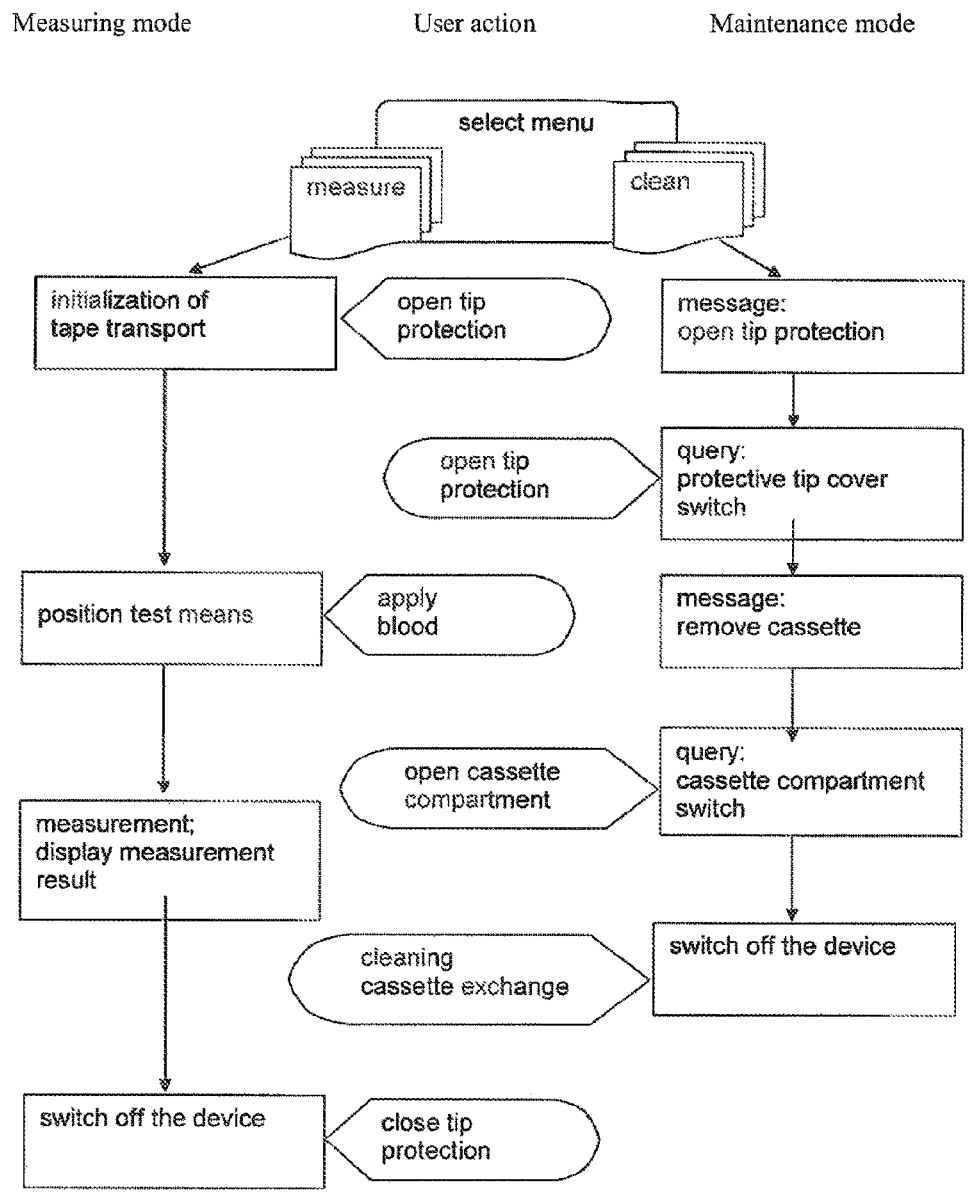
FIG. 3 shows a flow diagram to illustrate one embodiment of a process employing the measuring mode and maintenance mode of the blood sugar measuring device of the present invention.

The process control shown in FIG. 3 uses simple measures to enable an alternative mode between measuring and maintenance while reducing the number of required operating steps and user actions whereby a loss of test means is largely avoided.

As shown in the left part of the diagram in FIG. 3, a measuring cycle can be started by the user by opening the tip protection (protective cover 26) without the need to operate additional start buttons. This ensures a very rapid availability of the system. The menu selection "measuring" can, however, also be selected via the operating buttons 18, 20 as an alternative start actuation.

The unused test fields 44 remain screened against environmental influences such as light, humidity and dirt on the supply spool 40 that is screened towards the outside until the measuring cycle is started. The positioning of the test fields at the application site 46 is then controlled by a tape transport in which control marks applied to the test tape 38 are registered during an initialization phase in order to enable a defined tape advance. In this case the possibility of winding back is not provided due to the complication of the apparatus and could lead to undefined states of the test means. Subsequently blood is applied to the test field 44 positioned above the measuring tip as the next user action. Then a measurement result obtained by means of the measuring unit 31 can be displayed on the display 22. The measuring cycle is ended in a simple manner by the user by closing the tip protection 26 whereupon the used test field 44 is disposed of on the take-up spool 42 by further tape transport and the device is switched off. Such a measuring cycle can be repeated until all stored test fields 44 are used before a cassette replacement is necessary.

If in the measuring mode an unscheduled but monitored device access occurs and in particular if the cassette compartment 34 is opened, the control device discards the current test for safety reasons in order to exclude a possible falsification of the measured value. In this case it must be borne in mind that the device must also be designed to be operated by laymen and that a false measurement result can lead to serious false diagnoses.

This must be differentiated from a necessary access to the inside of the device in order to clean it or to fulfill other service functions or for demonstration purposes. In such a case a disadvantageous loss of a test means or test field 44 should be avoided. For this purpose the control device can be put into a maintenance mode by a defined control intervention as shown in the right part of the diagram of FIG. 3.

The control intervention is realized by the menu point "clean" of a software menu which the user can simply select by the operating key 20. This key is designed as a "softkey" and can thus execute different functions depending on a screen display.

As soon as the maintenance mode has been initiated, the sensor signals which occur when the tip protection 26 or the cassette compartment 34 are opened, are ignored or no longer interpreted as a start actuation so that an automatic tape transport no longer occurs. Thus the start of a measuring cycle is blocked and an unintentional loss of test means is prevented.

The user can then be prompted to carry out certain actions via the screen 22. After the tip protection 26 and the cassette compartment cover 36 are opened, the device is switched off. The user can remove the cassette 12, clean the interior of the device and in particular the measuring optics 31, replace the cassette and reclose the cassette compartment and tip protection. The device 10 is then on standby for the measuring mode.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method for controlling a hand-held analysis device for analyzing a body fluid, the device comprising a tape drive unit for advancing test fields, an electronic control device configured to automatically provide at least one test field on a test means comprising a plurality of test fields for single use arranged on a wound test tape in consecutive measuring cycles when the electronic control device is in a measuring mode, each measuring cycle being triggered by a start actuation, and a sensor for monitoring and outputting a signal responsive to the start actuation, the method comprising the step of:

putting the electronic control device into a maintenance mode by a defined control intervention, wherein the sensor signal is ignored when the electronic control device is put in the maintenance mode, thereby suspending the automatic provision of at least one of the plurality of test fields on the test means inserted into the hand-held analysis device during the maintenance mode, and wherein the defined control intervention is manually activating a switch comprising a softkey or control button of the hand-held analysis device to thereby put the electronic control device of the hand-held analysis device into the maintenance mode.

2. The method according to claim 1, further wherein the start of a measuring cycle is blocked during the maintenance mode even in the case of a start actuation.

3. The method according to claim 1, wherein the device can be cleaned or test means can be exchanged in the maintenance mode without a loss of test means.

4. The method according to claim 1, wherein putting the electronic control device into the maintenance mode is performed by selecting the maintenance mode via a software menu of the electronic control device.

5. The method according to claim 1, wherein the start actuation comprises a predetermined operation of a component of the analysis device, the operation being recognized by the electronic control device.

6. The method according to claim 1, wherein the test means are protected in a housing of the hand-held analysis device against environmental influences.

7. The method according to claim 1, wherein the start actuation for a measuring cycle comprises opening a protective cover of the hand-held analysis device whereupon a test means is provided for access by the user.

8. The method according to claim 1, wherein during the measuring mode the test means are automatically transported by a tape drive unit to at least one predetermined position and the automatic transport of test means is suspended during the maintenance mode.

9. The method according to claim 1, wherein the test means are transported from a store of test means to an application site and transported to a test means waste during a measuring cycle.

10. The method according to claim 1, wherein a test tape furnished with a plurality of analytical test fields as test means is used and the test tape is wound up in sections to provide the test means.

11. The method according to claim 1, wherein the test means can be exchanged in a compartment of the device, the test means having the form of a magazine or a cassette, the test means being activated by a start actuation and discarded during the measuring mode when the compartment of the device is opened.

12. A hand-held analysis device for analyzing a body fluid, the device comprising:

a device housing;

a tape drive unit for advancing test fields on a test means comprising a plurality of test fields for single use arranged on a wound test tape;

a measuring unit for obtaining measurement results from the test fields;

an electronic control device for automatically providing at least one test field on the wound test tape in consecutive measuring cycles where each measuring cycle can be triggered in a measuring mode of the electronic control device by a start actuation and where the test tape is wound up in sections to provide the at least one test field on the test means; and a sensor for monitoring and outputting a signal responsive to the start actuation;

wherein the electronic control device can be put into a maintenance mode by a defined control intervention when the wound test tape is present in the hand-held device, wherein the sensor signal is ignored when the electronic control device is put into the maintenance mode, thereby suspending the automatic provision of the at least one test field on the wound test tape, and wherein the defined control intervention is manually activating a switch comprising a softkey or control button of the hand-held analysis device.

* * * * *